United States Patent [19]
Sullivan

[11] Patent Number: 5,975,895
[45] Date of Patent: Nov. 2, 1999

[54] STROBE LIGHT CURING APPARATUS AND METHOD

[75] Inventor: Jerry Sullivan, Mahwah, N.J.

[73] Assignee: Coltene/Whaledent, Mahwah, N.J.

[21] Appl. No.: 08/968,188

[22] Filed: Nov. 12, 1997

[51] Int. Cl.[6] .................................................. A61L 1/00
[52] U.S. Cl. ........................................................... 433/29
[58] Field of Search .................. 433/29, 229; 250/492.1, 250/493.1, 504 H

[56] References Cited

U.S. PATENT DOCUMENTS

| | | | |
|---|---|---|---|
| 4,229,658 | 10/1980 | Gonser | 250/504 H |
| 4,309,617 | 1/1982 | Long | 250/504 H |
| 4,385,344 | 5/1983 | Gonser | 433/29 |
| 4,450,139 | 5/1984 | Bussiere et al. | 433/29 |
| 4,538,070 | 8/1985 | Herold et al. | 250/504 R |
| 4,582,998 | 4/1986 | Gonser et al. | 250/492.1 |
| 4,790,919 | 12/1988 | Baylor, Jr. | 204/182.8 |
| 4,874,315 | 10/1989 | Featherstone et al. | 433/215 |
| 5,049,068 | 9/1991 | Sterrett et al. | 433/9 |
| 5,092,773 | 3/1992 | Levy | 433/224 |
| 5,147,204 | 9/1992 | Patten et al. | 433/229 |
| 5,151,031 | 9/1992 | Levy | 433/226 |
| 5,169,318 | 12/1992 | Levy | 433/226 |
| 5,171,150 | 12/1992 | Levy | 433/226 |
| 5,290,169 | 3/1994 | Friedman et al. | 433/29 |
| 5,388,987 | 2/1995 | Badoz et al. | 433/29 |
| 5,397,892 | 3/1995 | Abdelqader | 250/227.24 |
| 5,449,703 | 9/1995 | Mitra et al. | 522/57 |
| 5,521,392 | 5/1996 | Kennnedy et al. | 250/492.1 |
| 5,634,711 | 6/1997 | Kennedy et al. | 433/29 |

FOREIGN PATENT DOCUMENTS

3436830 A1   4/1986   Germany ................. 433/29

Primary Examiner—John J. Wilson
Assistant Examiner—Patraick A. Hismier
Attorney, Agent, or Firm—Helfgott & Karas, PC.

[57] ABSTRACT

A strobe light curing apparatus which includes trigger electronics for producing a series of pulses at a predetermined frequency. A flash lamp is coupled to the trigger electronics for producing flashing light according to the series of pulses. A reflector is further disposed from the lamp at a first predetermined distance for reflecting and focusing the flashing light at a second predetermined distance.

19 Claims, 3 Drawing Sheets

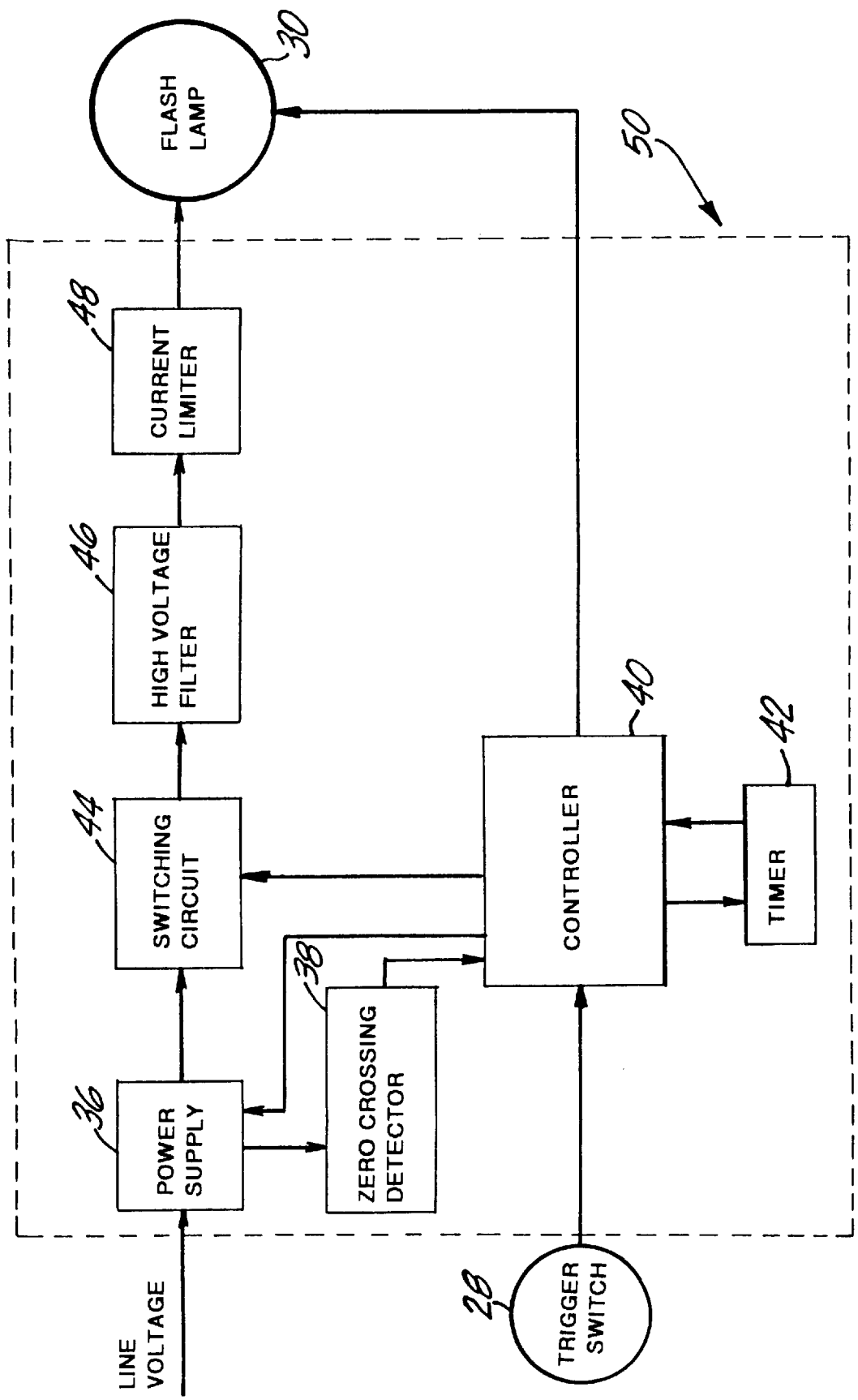

STROBE LIGHT CURING APPARATUS AND METHOD

BACKGROUND OF THE INVENTION

1. Field of the Invention

The present invention relates in general to dental instruments and procedures, and, in particular, to an apparatus or method for curing dental composites which incorporates the use of a strobe light.

2. Description of Prior Developments

Dental composites are well known materials utilized in a variety of dental procedures. For example, these materials are utilized in restoration work as well as for filling in teeth after root canals or other type of procedures requiring drilling. Several different dental composites are available in today's market, which are sold under the trade names of BRILLIANT LINE, Z-100, TPH, CHARISMA, and HERCULITE & BRODIGY.

Dental composites are typically formed from a liquid and powder component, which are mixed together to form a paste. The paste has a consistency which enables it to be sufficiently workable and self supporting to be applied to an opening or cavity in a tooth. The liquid component can be composed of phosphoric acid and water, while the powder component can be composed of ceramic materials including cordite, silica or silicium oxide.

Dental composites when utilized are applied to an opening or cavity in a tooth of the patient. After the composite is applied, it must be cured in order to form a permanent bond to the tooth. During curing, the liquid component evaporates, which causes the composite to harden. In the past, dental composites have been cured by normal air drying. However, conventional air curing tends to take a long period of time, which often can inconvenience the patient.

Other methods have been developed in order to reduce the curing time of these dental composites. For example, light curing has become popular in field of dentistry for fabricating dentures as well as for curing composites. According to this trend, light curing lamps have been developed for dental curing applications. An example of such a curing lamp is disclosed in U.S. Pat. No. 5,397,892, issued Mar. 14, 1995, to Abdelqader, the same inventor herein. These curing lamps utilize a quartz halogen lamp that includes a "glowing filament".

However, improvements on these curing lamps appear to be needed. One reason is that these type of lamps produce a lot of light in the infrared range, which is not useful for curing dental composites. Further, since these lamps are continuous, a large amount of radiant energy can be produced, which may irritate or harm the patient. Another undesirable result of the large amount energy produced by these lamps is that the composite may be overheated. Over-heating the composite is undesirable since it can cure the composite too fast and thus cause excessive shrinkage.

Another method of light curing has been developed which utilizes pulsed laser light. The use of pulsed laser light for dental as well as medical applications is disclosed in U.S. Pat. No. 5,171,150, issued Dec. 15, 1992, to Levy. However, utilizing pulsed laser light for curing dental composites also suffers from similar drawbacks, as previously described in regard to the continuous light curing lamps. The lasers utilized in these applications also produce a lot of radiation and heat, which as previously described can irritate or possibly harm the patient, and overheat the composite as well. Also, utilizing lasers may be more expensive than using a conventional lamp or light source.

In view of the above, a need therefor exists for a curing apparatus or method in which dental composites can be cured effectively in a shorter period of time than conventional air curing. A further need exists for a curing apparatus and method that is less likely to cause irritation or overheat the dental composite being cured.

SUMMARY OF THE INVENTION

The present invention has been developed to fulfill the needs noted above and therefore has as an object the provision of a curing apparatus or method which is capable of curing dental composites effectively in a shorter period of time than conventional air curing.

Another object of the invention is to provide a curing apparatus or method which is less likely to cause irritation to the patient.

Another object of the invention is to provide a curing apparatus or method which is less likely to overheat the dental composite during curing.

Still another object of the invention is to provide a curing apparatus or method which produces a higher percentage of light that is useful for curing dental composites.

These and other objects are met with an apparatus in accordance with the present invention which includes trigger electronics for producing a series of pulses at a predetermined frequency. A flash lamp is coupled to the trigger electronics for producing flashing light according to the series of pulses. A reflector is further disposed from the lamp at a first predetermined distance for reflecting and focusing the light at a second predetermined distance.

The trigger electronics includes a switching circuit coupled to both the lamp and a controller. The controller switches the switching circuit on and off at the predetermined frequency in order to produce the series of pulses. Further, the controller switches the switching circuit on and off for a predetermined period of time, which is provided by a timer. The trigger electronics further include a high voltage filter and a current limiter coupled between the lamp and switching circuit.

The present invention is also directed to a method for curing dental composites including the following steps. Producing a series of pulses at a predetermined frequency. Applying the pulses to a flash lamp for producing flashing light according to the pulses. Reflecting the light onto an area containing the dental composites through a fiber optic bundle.

The aforementioned objects, features and advantages of the invention will, in part, be pointed out with particularity, and will, in part, become obvious from the following more detailed description of the invention, taken in conjunction with the accompanying drawings, which form an integral part thereof.

BRIEF DESCRIPTION OF THE DRAWINGS

In the drawings:

FIG. 4 is a block diagram of the electronics for the strobe light curing apparatus according to the present invention.

DETAILED DESCRIPTION OF THE PREFERRED EMBODIMENTS

The present invention is directed to a strobe light curing apparatus or method which is capable of more effectively curing dental composites than conventional methods. The present invention achieves these objectives by incorporating a strobe light. A strobe light includes a flash lamp that produces high intensity short duration light pulses by electric discharge in a gas. Thus, according to the present invention, instead of using a conventional light bulb which typically includes a "glowing filament", a gas filled flash lamp is utilized.

According to the present invention, the use of a strobe light for curing dental composites has a number of advantages over the use of conventional bulbs. First of all, the flash lamp which is gas filled included in the present invention produces less light in the infrared region than conventional glowing filament bulbs. Therefore, the present invention produces more light in the visible range, which is more useful for curing dental composites.

Further, since a strobe light flashes on and off, it produces less radiant energy than either the continuous light or laser light sources. Thus, the use of a strobe light in the present invention prevents the dental composite from being overheated. This enables the dental composite to be heated more slowly and thus prevents the problem of excessive shrinking. However, the strobe light still produces enough energy to cure the dental composite in a substantially shorter period of time than conventional air curing.

Moreover, since a strobe light produces less heat than continuous lamps or lasers, the patient is less likely to be irritated or harmed during the curing process. Further, since the strobe light is flashed off and on as opposed to being continuously turned on, the flash lamp itself would have a longer life and thus requires less replacement.

Figure 1:
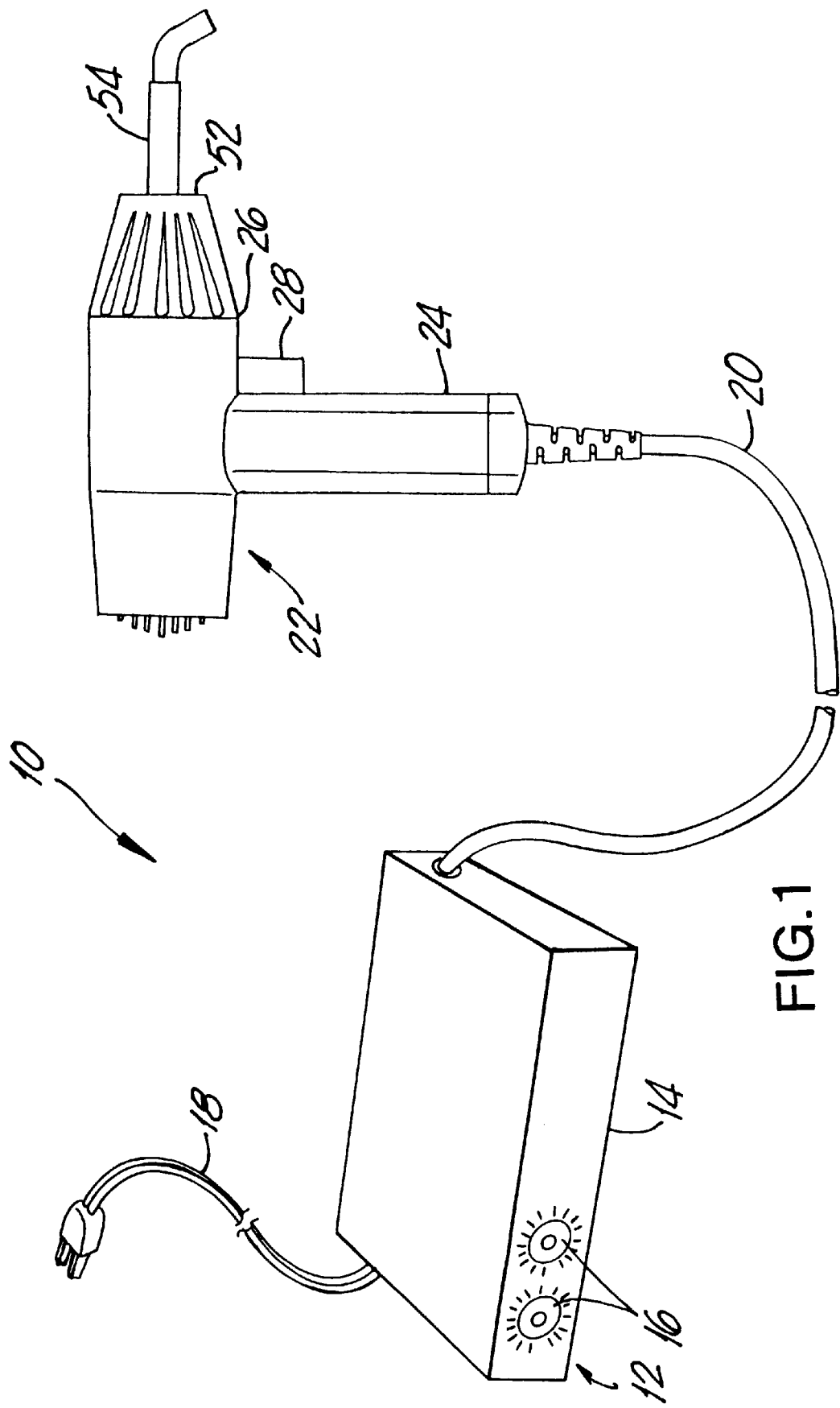
FIG. 1 shows an embodiment of a strobe light curing apparatus according to the present invention.

An embodiment of the present invention will now be described in conjunction with the drawings beginning with FIG. 1. As can be seen, the strobe light curing apparatus 10 in this particular embodiment has a multi-piece configuration including a curing lamp 22 and a control box 12. The curing lamp 22 houses the flash lamp and associated elements for providing the strobe light effect. While the control box 12 houses the electronics for triggering the curing lamp 22. A cable 20 interconnects the curing lamp 22 and control box 12 which carries electrical signals between the two.

The curing lamp 22 consists of a housing 24,26 which preferably has a hand held gun configuration. Such a configuration is desirable since it makes it easy to point and hold the curing lamp 22. The housing includes a handle portion 24 as well as a barrel portion 26. Disposed in the front surface of the handle 24 is a trigger switch 28 for both activating and deactivating the curing lamp 22.

Disposed in the front of the barrel 52 is a fiber optic bundle 54 which transfers the light produced inside the lamp 22 to an external area containing the dental composite to be cured. The use of the fiber optic bundle 54 is desirable since it can be placed in areas that may be difficult to reach such as a patient's mouth.

The control box 12 consists of a housing 14 which preferably has a rectangular configuration. Disposed on the front surface of the housing 14 are controls 16, which can be embodied either by rotating knob controls or push button controls. The controls 16 are utilized to adjust such parameters as the power output and timing of the curing lamp 22. Disposed in one side surface of the housing 14 is a power cable 18, which provides line power to the control box 12. While disposed in the other side surface of the housing 14 is one end of the signal cable 20.

Figure 2:
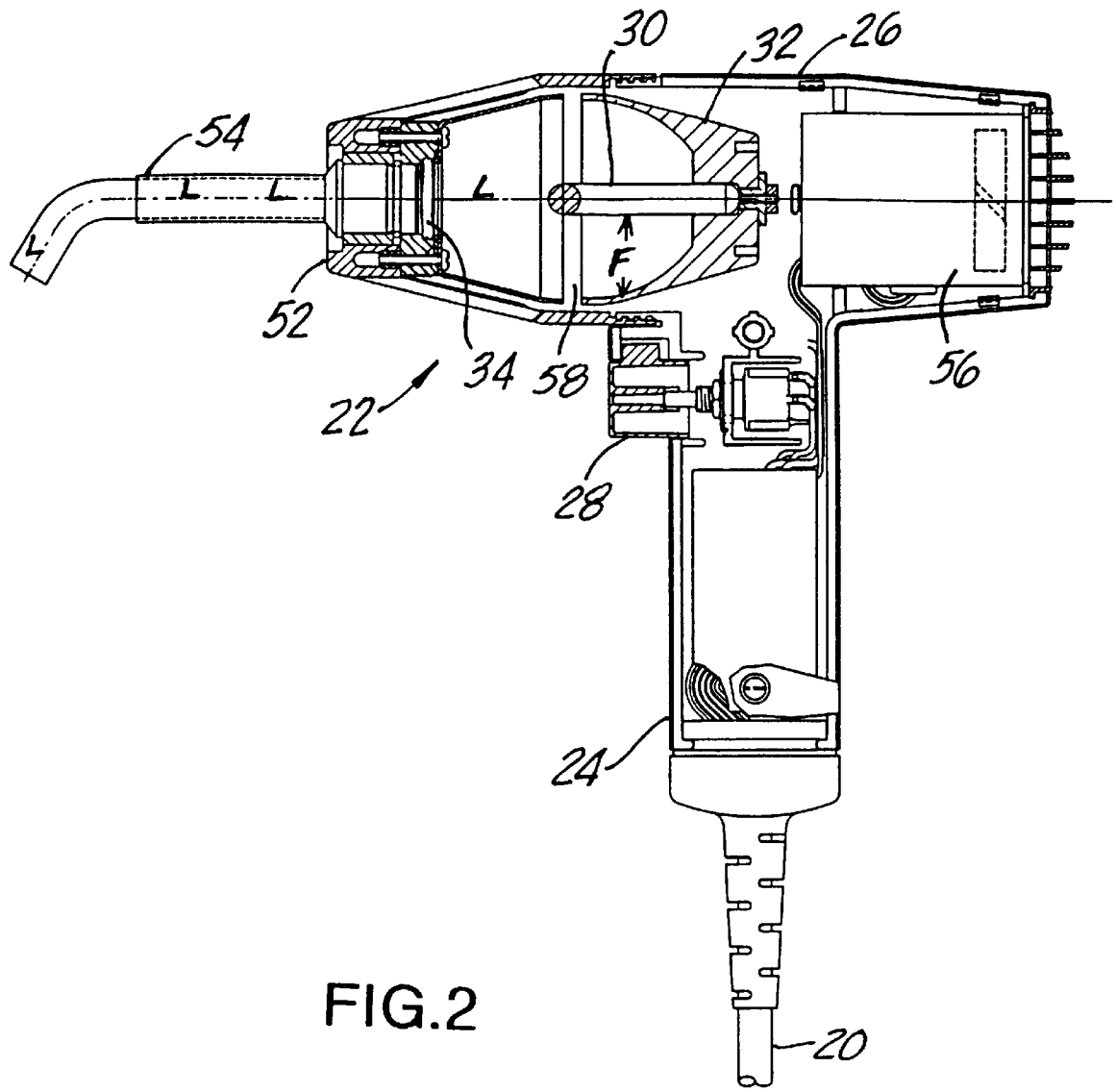
FIG. 2 shows an inner configuration of the strobe light curing lamp of FIG. 1.

An inner view of the curing lamp 22 according to the present invention is shown in FIG. 2. The other end of the signal cable 20 is disposed within a lower surface of the handle 24. The signal cable 20 includes wires which are separately connected to the trigger 28, flash lamp 30 (not shown) and fan 56.

As can be seen, the flash lamp 30 is disposed within the barrel portion 26 and is secured therein by a bracket 58. The flash lamp 30 as previously described is a gas filled device, which produces high intensity short duration light pulses. An example of a commercially available flash lamp is an ELEVAM MFT-112M. The flash lamp 30 is the element which actually produces the strobe light effect L when excited by a series of electrical pulses known as trigger pulsed voltage signals. The flash lamp 30 flashes off and on L according to the trigger pulsed voltage signals provided.

The trigger pulsed voltage signals are produced by the trigger electronics, which will be described in detail later. The trigger pulse voltage signals have a predetermined pulse rate which correspond to the flash rate of the strobe light. It is preferred according to the present invention, that the strobe light has a flash rate of 15–50 flashes per minute.

Disposed also in the barrel 26 is a reflector 32, which is utilized to reflect or redirect the light L produced by the flash lamp 30 in a predetermined direction. In this particular embodiment, the predetermined direction is parallel with the length of the barrel 26, which enables the light L to be reflected toward the front of the barrel 26 to the fiber optic bundle 54. The reflector 32 preferably should be configured so that the light L is reflected through the center of the barrel 26. This ensures that the maximum amount of light L is transferred through the fiber optic bundle 54 for curing.

Further, the reflector 32 is disposed from the flash lamp 30 at a predetermined distance known as a focal length F. The focal length F is a significant parameter since it determines the distance from the reflector 32 at which the majority of the light L is focused. In selecting the focal length F, a number of factors are considered including the length of the barrel 26 and the smallest proximity at which the curing lamp 22 can be safely placed next to the patient. It is preferable that the focal length F is selected to be in a range of 15–50 milli-meters.

It is also preferable that the reflector 32 is configured to reflect the wavelength of light most useful for curing dental composites. The preferred wavelength for dental composite curing is in the visible range of 400–525 nano-meters. The reflector 32 can be configured to selectively reflect this range of wavelengths by including additional layers of optical coatings.

Disposed in front of the reflector 32 is an output band filter 34. The output band filter 34 is also disposed in a front surface of the barrel 52 adjacent to the fiber optic bundle 54, as shown. The band filter 34 is configured to only pass the wavelength of light in the above mentioned optimum range of 400–525 nano-meters range. Thus, the filter 34 further ensures that the light L leaving the lamp 22 during operation is in this desired range.

The fiber optic bundle 54 is also disposed in the front surface of the barrel 52, as shown. As previously described, fiber optic bundle 54 transfers the light L from the barrel 26 to the area containing the dental composite, such as a patient's mouth. Disposed in the rear portion of the barrel 26 is the fan 56. The fan 56 cools the internal components of the lamp 22 in order to prevent overheating.

During operation, the curing lamp 22 will operate as follows. A user will hold the curing lamp 22 so that the end of the fiber optic bundle 54 is over the area containing the dental composite. The user then depresses the trigger 28, which causes a signal to be transmitted to the control box via the cable 20. In response, a predetermined number of trigger pulse voltage signals are produced by the trigger electronics in the control box, which are transmitted back to the curing lamp 22 via the cable 20.

The trigger pulse voltage signals then cause the flash lamp 30 to be flashed of and on producing the strobe light L. The strobe light L radiates toward the reflector 32, which reflects the light L through the band pass filter 34 and fiber optic bundle 54.

The flash lamp 30 will continue to produce the strobe light as described above until the predetermined number of trigger pulse voltage signals is exhausted. However, this operation can be terminated before the trigger pulse voltage signals are exhausted by the user depressing the trigger 28 again. When the trigger 28 is depressed for the second time, another signal is transmitted to the control box, which causes the trigger electronics to stop producing any further trigger pulse voltage signals.

Figure 3:
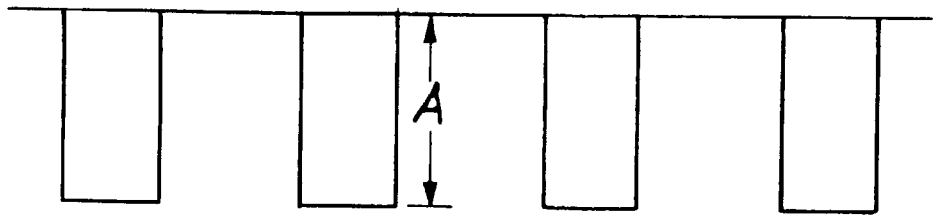
FIG. 3 is a diagram of trigger pulse voltage signals according to the present invention.

A diagram of the trigger pulse voltage signals according to the present invention is shown in FIG. 3. As previously described, the trigger pulse signals have a predetermined pulse rate or frequency of 15–50 pulses per minute, which provides a flash rate of the same. As can be seen, the trigger pulse voltage signals are a series of pulses having a predetermined voltage level A.

The voltage level A of the trigger pulses should be in the range necessary to excite conventional flash lamps, which is in the range of −2 to −18 Kilo-volts per pulse. Further, each trigger pulse should have a maximum flash energy of 10–300 Joules. The maximum flash energy is the optimal energy range for curing dental composites where the strobe light produced is less likely to cause irritation or overheat the composite. This energy range provides a total light output for the apparatus in the range of 800–2500 milli-Watts per $cm^2$.

A block diagram of the electronics for the strobe light curing apparatus according to the present invention is shown in FIG. 4. The elements enclosed by the dotted line represent the trigger electronics 50 housed in the control box, while the elements outside the dotted line are housed in the curing lamp.

As previously described, the trigger electronics 50 produce the trigger pulse voltage signals for exciting the flash lamp 30 in order to produce the strobe light. The trigger electronics include a power supply 36 which receives the line voltage brought into the control box. The power supply 36 includes a step-up transformer, which increases the amplitude of the line voltage in order to realize the large amplitude requirements of the trigger pulse voltage signals. The power supply may also include other well known features such as a capacitor output filter or a voltage regulator.

Coupled to one output of the power supply 36 is a switching circuit 44, which is utilized to produce the trigger pulse voltage signals. This is accomplished by selectively switching the switching circuit 44 on and off in a predetermined fashion, which essentially modulates the output of the power supply 36. The switching circuit 44 may be embodied by an electrical relay device.

Coupled between the switching circuit 44 and one side of the flash lamp 30 is both a high voltage filter 46 and current limiter 48, which provide circuit protection for the lamp 30. The high voltage filter 46 passes only the desired high voltage levels to the lamp 30, while the current limiter 48 limits the current to the flash lamp 30. The particular design of these elements 46, 48 will depend on the particular requirements of the flash lamp 30 utilized.

The trigger electronics 50 further include a controller 40 for performing various control functions. The controller 40 can be embodied by any general purpose micro-controller, which is capable of being programmed to perform the following described functions.

The controller 40 has an output coupled to the power supply 36 which enables it to adjust the output signal of the power supply. Coupled between the power supply 36 and an input of the controller 40 is a zero crossing detector 38. The zero crossing detector 38 enables the controller 40 to monitor the output signal of the power supply 36. The zero crossing detector 38 will provide a signal to the controller 40 anytime the output signal of the power supply 36 crosses the zero potential point. The zero crossing detector 38 can be embodied by a comparator circuit which compares the output of the power supply 36 to a zero potential.

The controller 40 has another output coupled to the switching circuit 44 which enables it to control the switching circuit 44 during operation. The controller 44 controls the switching circuit 44 by providing appropriate signals to switch the switching circuit 44 on and off in order to produce the trigger pulse voltage signals.

The signals provided to the switching circuit 44 by the controller 40 have a predetermined frequency as well as a predetermined number. The predetermined frequency of these signals will correspond to the pulse rate of the trigger pulse voltage signals, which as previously described is in the range 15–50 pulses per minute. While the predetermined number of these signals will correspond to the predetermined number of the trigger pulse voltage signals provided to the flash lamp 30 during operation, as previously described.

Coupled to another input and output of the controller 40 is a timer 42. The timer 42 provides the timing for the signals produced by the controller which are utilized to switch the switching circuit 44 on and off during operation. Coupled to another input of the controller 40 is the trigger switch 28, which is utilized to activate and deactivate the controller 40.

Coupled to another output of the controller 40 is the other side of the flash lamp 30. The controller 40 during operation utilizes this particular output to provide a reference potential to this side of the flash lamp 30.

During operation, the controller normally is in a deactivated state. When a user depresses the trigger switch 28, the controller 40 then is switched to the activated state. The controller 40 being activated causes it to provide a reference potential to the other side of the flash lamp 30.

Further, the controller 40 when activated turns on the timer 42. In response, the timer produces a timing signal for a predetermined period of time. For the duration of this timing signal, the controller 40 produces the signals that switches the switching circuit 44 on and off, as previously described. The trigger pulse voltage signals are then produced, which are transmitted to one side of the lamp 30 through the high voltage filter 46 and current limiter 48. This causes the flash lamp 30 to produce the strobe light for the duration of the timing signal produced by the timer 42.

The lamp 30 will continue to strobe until either the timing signal expires or the user depresses the trigger switch 28 again. If the trigger switch 28 is depressed again, the controller 40 turns the timer 42 off causing the timing signal to be no longer produced. In response, the controller 40 no longer produces the signals used to switch the switching circuit 44 and is placed in the deactivated state. This causes the flash lamp 30 to stop strobing.

In the case where the timing signal is allowed to expire after the predetermined time period, the timer 42 turns off which again also stops the flash lamp 30 from strobing, as described above. In either case, the controller 40 remains in the deactivated state until the trigger switch 28 is depressed again.

The controller 40 when activated also continually controls the output of the power supply 36. This is necessary in the event the line voltage drops, which can cause the amplitude of the trigger pulse voltage signals to fall below the required level to excite the flash lamp 30. Any time the controller 40 receives a signal from the zero crossing detector 38, it automatically raises the output of the power supply 36 to the level required to excite the flash lamp 30. Therefore, the amplitudes of the trigger pulse voltage signals are kept at this required level.

There has been disclosed heretofore the best embodiment of the invention presently contemplated. However, it is to be understood that various changes and modifications may be made thereto without departing from the spirit of the invention.

What is claimed is:

1. A strobe light dental curing apparatus, comprising:

trigger electronics for producing a series of pulses at a predetermined frequency;

a flash lamp coupled to said trigger electronics for producing flashing light according to said series of pulses; and a reflector disposed from said lamp at a first predetermined distance for reflecting and focusing said flashing light at a second predetermined distance wherein said reflector is configured to reflect light in the wavelength range of 400–525 nano-meters.

2. The apparatus of claim 1, wherein said trigger electronics includes:

a switching circuit coupled to said lamp; and a controller coupled to said switching circuit for switching said switching circuit on and off at said predetermined frequency in order to produce said series of pulses.

3. The apparatus of claim 2, wherein said controller switches said switching circuit on and off for a predetermined period of time.

4. The apparatus of claim 3, wherein said trigger electronics further includes a timer coupled to said controller for providing said predetermined period of time.

5. The apparatus of claim 2, wherein said trigger electronics further includes a high voltage filter coupled between said lamp and said switching circuit.

6. The apparatus of claim 2, wherein said trigger electronics further includes a current limiter coupled between said lamp and said switching circuit.

7. The apparatus of claim 1, which further includes a band pass filter disposed in front of said reflector.

8. The apparatus of claim 7, wherein said band pass filter is configured to pass light in the wavelength range of 400–525 nano-meters.

9. The apparatus of claim 1, wherein said predetermined frequency of said series of pulses is 15–50 pulses per minute.

10. The apparatus of claim 1, wherein each of said series of pulses has a voltage level in the range of −2 to −18 Kilo-volts.

11. The apparatus of claim 1, wherein each of said series of pulses has a flash energy in the range of 10–300 Joules.

12. The apparatus of claim 1, wherein said first predetermined distance is in a range of 15–50 milli-meters.

13. The apparatus of claim 1, which further includes a fiber optic bundle disposed in front of said reflector for transferring the light from said apparatus.

14. A strobe light dental curing apparatus, comprising:

trigger electronics for producing a series of pulses at a predetermined frequency;

a flash lamp coupled to said trigger electronics for producing flashing light according to said pulses; and a reflector disposed from said lamp at a predetermined orientation for reflecting the flashing light in a predetermined direction wherein said reflector is configured to reflect light in the wavelength range of 400–525 nano-meters.

15. The apparatus of claim 14, wherein said predetermined frequency of said series of pulses is 15–50 pulses per minute.

16. The apparatus of claim 14, which further includes a housing including a handle portion and a barrel portion, wherein said lamp and said reflector is disposed in said barrel, and said predetermined direction is parallel with a length of said barrel.

17. A method for curing dental composites, comprising the steps of:

producing a series of pulses at a predetermined frequency;

applying said pulses to a flash lamp for producing flashing light according to said pulses; and reflecting said flashing light onto an area containing said dental composites wherein said reflector is configured to reflect light in a wavelength range of 400–525 nano-meters.

18. The method of claim 17, wherein said predetermined frequency of said series of pulses is 15–50 pulses per minute.

19. A strobe light curing apparatus, comprising:

a trigger electronics having a power supply with an output signal for producing a series of pulses at a predetermined frequency;

a zero crossing detector coupled to said trigger electronics for monitoring the output signal of said power supply;

a flash lamp coupled to said trigger electronics for producing flashing light according to said series of pulses; and a reflector disposed from said lamp at a first predetermined distance for reflecting and focusing said flashing light at a second predetermined distance wherein said reflector is configured to reflect light in the wavelength range of 400–525 nano-meters.

* * * * *